US007282130B2

(12) United States Patent
Flory

(10) Patent No.: US 7,282,130 B2
(45) Date of Patent: Oct. 16, 2007

(54) APPARATUS AND METHOD FOR CONTROL OF BIOPOLYMER TRANSLOCATION THROUGH A NANOPORE

(75) Inventor: Curt A. Flory, Los Altos, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 865 days.

(21) Appl. No.: 10/355,347

(22) Filed: Jan. 31, 2003

(65) Prior Publication Data

US 2004/0149580 A1 Aug. 5, 2004

(51) Int. Cl.
*G01N 27/447* (2006.01)
(52) U.S. Cl. .................. 204/600; 204/450; 435/287.1; 435/287.2
(58) Field of Classification Search ............... 204/450, 204/600, 403.01–403.15, 775–794.5; 435/287.1–287.2
See application file for complete search history.

(56) References Cited

U.S. PATENT DOCUMENTS

| 6,051,380 | A | 4/2000 | Sosnowski et al. |
| 6,245,508 | B1 | 6/2001 | Heller et al. |
| 6,627,067 | B1 | 9/2003 | Branton et al. |
| 2002/0119455 | A1 | 8/2002 | Chan |
| 2002/0182627 | A1* | 12/2002 | Wang et al. .................. 435/6 |
| 2002/0197618 | A1 | 12/2002 | Sampson |
| 2004/0033492 | A1* | 2/2004 | Chen .............................. 435/6 |

FOREIGN PATENT DOCUMENTS

| WO | WO 02/42496 A2 | 5/2002 |
| WO | WO 03/000920 A2 | 1/2003 |
| WO | WO 03/003446 A2 | 1/2003 |

OTHER PUBLICATIONS

Li et al., "Ion-Beam Sculpting at Nanometre Length Scales", (2001), Macmillan Magazine Ltd., vol. 412, pp. 166-169.
Akeson et al., "Microsecond Time-Scale Discrimination among Polcytidylic Acid, Poladenylic Acid, and Polyurdylic Acid as Homopolymers or as Segments within Single RNA Molecules", (1999), Biophysical Journal, vol. 77, pp. 3227-3233.
Kasianowicz et al., "Characterization of Individual Polynucleotide Molecules using a Membrane Channel", (1996), Proc. Natl. Acad. Sci. USA, vol. 93, pp. 13770-13773.
European Search Report Dated: Feb. 27, 2004.

* cited by examiner

*Primary Examiner*—Nam Nguyen
*Assistant Examiner*—Jeffrey Barton

(57) ABSTRACT

The present invention provides an apparatus and method for controlling the movement of a biopolymer translocating a nanopore. The invention provides a first electrode, a second electrode adjacent to the first electrode, a third electrode adjacent to the second electrode and a fourth electrode adjacent to the third electrode. The first electrode is in electrical connection with the third electrode to define a first set of electrodes and the second electrode is in electrical connection with the fourth electrode to define a second set of electrodes. A DC voltage and radio frequency voltage is applied to the first set of electrodes while an opposite DC voltage and phase shifted radio frequency voltage is applied to the second set of electrodes to produce an electric field between the first set of electrodes and the second set of electrodes. The electric field is used to control the movement of a biopolymer translocating a nanopore. A method for controlling the movement of a biopolymer is also disclosed.

15 Claims, 7 Drawing Sheets

APPARATUS AND METHOD FOR CONTROL OF BIOPOLYMER TRANSLOCATION THROUGH A NANOPORE

TECHNICAL FIELD

The invention relates generally to the field of biopolymers and more particularly to an apparatus and method for control of the movement of a biopolymer during translocation of a nanopore.

BACKGROUND

Manipulating matter at the nanometer (nm) scale is important for many electronic, chemical and biological advances (See Li et al., "Ion beam sculpting at nanometer length scales", Nature, 412: 166–169, 2001). A number of sequencing techniques have been proposed at the micrometer and nanometer scale in response to the human genome project. These techniques have been largely developed to help characterize and understand expression of genes in vivo. A popular technique uses micro arrays and hybridization of cDNA to determine the presence or absence of a particular target gene. A target gene and probe are exposed in solution and bind if relative hybridization sequences match. Hybridization is indicative of the presence of the sequence or target gene. A dye may be employed with the target or probe to then determine existence and efficiency of hybridizations. The technique has been extended for use in determining the presence of single nucleotide polymorphism (SNP'S) in target cDNA. Micro arrays provide the promise of being able to accurately and concurrently screen for a variety of diseases in a particular patient. Theoretically, a patient should be able to enter a hospital, have blood taken, DNA extracted and genes sequenced. The sequencing methods provide for a genetic blue print of the individual. This provides patient specific information to doctors regarding susceptibility towards disease or existence of genetic abnormalities. A few major drawbacks of the micro array technique concern difficulty in manufacturing as well as the long time for effective hybridizations between probe and target (generally overnight to maintain high specificity). In addition, the large amounts of genomic DNA in a patient would require an inordinate amount of time and work. Therefore, new techniques are now being explored to more quickly sequence biopolymers. Systems that are on the nanoscale are both effective on resources (limited materials), but also may more closely mimic the processes already present in living cells (i.e. translocation processes). Therefore, nanopore technology has become a fundamental field area of interest to molecular biologists and biochemists alike.

It has been demonstrated that a voltage gradient can drive single-stranded biopolymers through a transmembrane channel, or nanopore (See Kasianowicz et al., "Characterization of individual polynucleotide molecules using a membrane channel", Proc. Natl. Acad. Sci. USA, 93: 13770–13773, 1996). During the translocation process, the extended biopolymer molecule will block a substantial portion of the otherwise open nanopore channel. This blockage leads to a decrease in the ionic current flow of the buffer solution through the nanopore during the biopolymer translocation. The passage of a single biopolymer can be monitored by recording the translocation duration and the blockage current, yielding plots with predictable stochastic sensing patterns. From the uniformly controlled translocation conditions, the lengths of the individual biopolymers can be determined from the translocation time. Furthermore, the differing physical and chemical properties of the individual bases of the biopolymer strand can in principle generate a measurable and reproducible modulation of the blockage current that allows an identification of the specific base sequence of the translocating biopolymer.

Another method for detecting a biopolymer translocating through a nanopore has been proposed. This technique is based upon quantum mechanical tunneling currents through the portion of the translocating strand as it passes between a pair of electrodes. Measuring the magnitude of the tunneling current would be an electronic method of detecting the presence of a translocating biopolymer, and if the conditions were adequately controlled and the measurements sufficiently sensitive, the sequence of constituent bases could also be determined. One of the primary motivations for this approach is that typical tunneling currents in scanning tunneling microscopes are on the order of 1–10 nanoamps, which is two to three orders of magnitude larger than the ionic currents observed during polymer translocation of 2 nanometer nanopores, as described above (See Kasianowicz et al., "Characterization of individual polynucleotide molecules using a membrane channel", Proc. Natl. Acad. Sci. USA, 93: 13770–13773, 1996).

Both of the techniques described above have major implementation challenges for detecting biopolymer translocation, characterizing the length of a stand, and ultimately performing sequencing of the constituent bases of the biopolymer. One of the primary difficulties is that the biopolymer is not constrained to pass through the center of the nanopore. Thus, there is an intrinsic variability between different translocation events, as well as potential variability during a single translocation as the possibility of lateral movement within the nanopore is assumed. The effects of this lateral displacement can be manifested in a number of ways for the two detection schemes described above.

For the first detection scheme that consists of measuring the magnitude of the reduced ionic current flow during translocation, lateral displacement of the translocating biopolymer can have two significant effects. First, if the biopolymer is moved away from the center of the nanopore, interactions with the walls of the nanopore itself would cause additional drag, causing the speed of the translocation to decrease. This variability would cause the measurement of the biopolymer length determined from the calibrated translocation time to be in error. In fact, it is not inconceivable that the translocating biopolymer could move far enough off the nanopore center that it could actually bind intermittently along the walls of the pore channel, either through molecular interactions or purely conformational binding of the biopolymer strand. The second significant effect that a lateral displacement of the translocating molecule would have is the potential change in the ionic blockage current. It is well known that the shape of an aperture can have significant effects on hydrodynamic flow. It is also self-evident that these effects become even more significant in the molecular flow regime, where the molecular size is on the order of the aperture. For this reason, it is expected that lateral displacement within the nanopore of the translocating biopolymer will cause significant variability in the magnitude of the measured ionic blockage current, making more difficult the job of differentiating the various bases by their blocking efficiencies, as described above.

For the second detection scheme, which consists of measuring quantum mechanical tunneling currents through the portion of the translocating biopolymer as it passes between a pair of electrodes, lateral displacement of the translocating strand can have two significant effects. As described for the first detection scheme, if the biopolymer is moved away from the center of the nanopore, interactions with the walls of the nanopore itself would cause additional drag, causing the speed of the translocation to decrease. This variability would cause the measurement of the biopolymer length determined from the calibrated translocation time to be in error. Secondly, it is well known that the tunneling current has an exponential dependence upon the height and width of the quantum mechanical potential barrier to the tunneling process. This dependence implies an extreme sensitivity to the precise location in the pore of the translocating molecule. Both steric attributes and physical proximity to the tunneling electrode could cause changes in magnitude of the tunneling current which would be far in excess of the innate differences expected between base-types under ideal conditions. For this reason, it is expected that lateral displacement within the nanopore of the translocating biopolymer will cause significant variability in the magnitude of the measured tunneling current, making more difficult the job of differentiating the various bases by their tunneling characteristics, as described above.

For all these reasons, variability of the lateral position of a biopolymer translocating a nanopore can cause significant problems, regardless of the detection scheme. A method of controlling the dynamics of the translocation process would provide many advantages over the present situation. These and other problems with the prior art processes and designs are obviated by the present invention. The references cited in this application infra and supra, are hereby incorporated in this application by reference. However, cited references or art are not admitted to be prior art to this application.

SUMMARY OF THE INVENTION

The invention provides a method and apparatus for controlling movement of a biopolymer through a nanopore. The apparatus of the invention comprises a first electrode, a second electrode adjacent to the first electrode, a third electrode adjacent to the second electrode and a fourth electrode adjacent to the third electrode. The first electrode and third electrodes are in electrical connection and define a first set of electrodes. The second electrode and the fourth electrode are in electrical connection and define a second set of electrodes. A DC voltage and radio frequency voltage is applied to the first set of electrodes, while an opposite DC voltage and phase shifted radio frequency voltage is applied to the second set of electrodes to produce an electric field between the first set of electrodes and the second set of electrodes. The electric field that is created is used to control movement of a biopolymer as it translocates through a nanopore. A plurality of electrodes or sets of electrodes may be used with the present invention. The electrodes may be positioned in a variety of arrangements or locations to define the nanopore or an optional substrate may be employed that comprises at least one nanopore.

The invention also provides a method for controlling the movement of a biopolymer through a nanopore, comprising applying a DC voltage and radio frequency voltage to a first set of electrodes, applying an opposite DC voltage and phase shifted radio frequency voltage to a second set of electrodes to produce an electric field between the first set of electrodes and the second set of electrodes to control movement of a biopolymer as it translocates through a nanopore. The method may comprise the use of one or more sets of electrodes or substrates.

BRIEF DESCRIPTION OF THE FIGURES

The invention is described in detail below with reference to the following figures.

DETAILED DESCRIPTION OF THE INVENTION

Figure 1A:
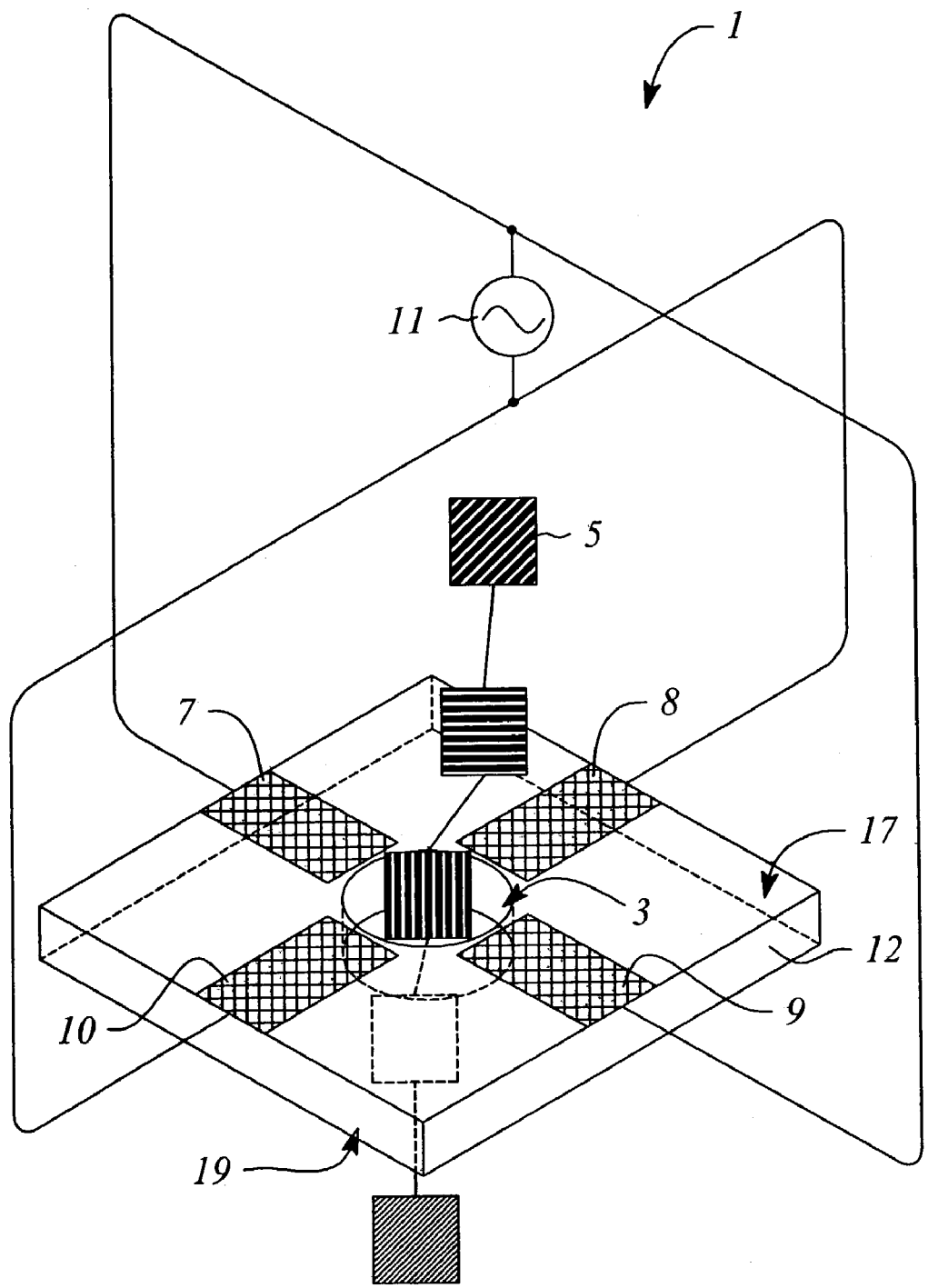
FIG. 1A is a schematic representation of a first embodiment of the present invention.

Before describing the present invention in detail, it is to be understood that this invention is not limited to specific compositions, method steps, or equipment, as such may vary. It is also to be understood that the terminology used herein is for the purpose of describing particular embodiments only, and is not intended to be limiting. Methods recited herein may be carried out in any order of the recited events that are logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

Unless defined otherwise below, all technical and scientific terms used herein have the same meaning as commonly understood by one of ordinary skill in the art to which this invention belongs. Still, certain elements are defined herein for the sake of clarity.

It must be noted that, as used in this specification and the appended claims, the singular forms "a", "an" and "the" include plural referents unless the context clearly dictates otherwise. Thus, for example, reference to "a biopolymer" includes more than one biopolymer, and reference to "a voltage source" includes more than one voltage source. In describing and claiming the present invention, the following terminology will be used in accordance with the definitions set out below.

A "biopolymer" is a polymer of one or more types of repeating units. Biopolymers are typically found in biological systems and particularly include polysaccharides (such as carbohydrates), peptides (which term is used to include polypeptides and proteins) and biopolymers as well as their analogs such as those compounds composed of or containing amino acid analogs or non-amino acid groups, or nucleotide analogs or non-nucleotide groups. This includes biopolymers in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in hydrogen bonding interactions, such as Watson-Crick type, Wobble type and the like. Biopolymers include single or multiple stranded configurations, where one or more of the strands may or may not be completely aligned with another.

A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a biopolymer) can hybridize with naturally occurring biopolymers in a sequence specific manner analogous to that of two naturally occurring biopolymers. Biopolymers include DNA (including cDNA), RNA, oligonucleotides, and PNA and other biopolymers as described in U.S. Pat. No. 5,948,902 and references cited therein (all of which are also incorporated herein by reference), regardless of the source. An "oligonucleotide" generally refers to a nucleotide multimer of about 10 to 100 nucleotides in length, while a "biopolymer" includes a nucleotide multimer having any number of nucleotides. A "biomonomer" references a single unit, which can be linked with the same or other biomonomers to form a biopolymer (e.g., a single amino acid or nucleotide with two linking groups one or both of which may have removable protecting groups).

The term "substrate" or "substrate surface" are synonymous and refer to the material an electrode may be attached, comprise or be embedded in.

The term "movement" shall have broad based meaning. The term shall include lateral, forward, backward, linear and sideways advancements or displacements of a biopolymer or portions of a biopolymer through a nanopore.

The term "in" refers to being "within" and/or a portion that may also be exterior to. For instance, a biopolymer "in" a nanopore may mean that the whole biopolymer is within the opening of the nanopore or only a small portion of the biopolymer is located near the nanopore with a substantial portion protruding exterior to the nanopore.

The term "nanopore" refers to any pore or hole between at least a pair of electrodes or a hole in a solid substrate. Nanopores can range in size and can range from 1 nm to around 300 nm. Most effective nanopores have been roughly 2–20 nm.

The term "translocation" or to "translocate" refers to movement from one side to another, or movement in a defined direction.

The term "portion" or "portion of a biopolymer" refers to a part, subunit, monomeric unit, portion of a monomeric unit, atom, portion of an atom, cluster of atoms, charge or charged unit.

The term "adjacent" refers to anything that is near, next to or adjoining. For instance, a nanopore may be near an electrode, it may be next to the electrode, or it may be adjoining the electrode. This would include spacing in linear, two-dimensional and three-dimensional space.

Referring now to FIGS. 1–2, the present invention provides a biopolymer translocation apparatus 1 that is capable of preventing lateral movement of a biopolymer 5 translocating a nanpore 3. The biopolymer translocation apparatus 1 comprises a first electrode 7, a second electrode 8, a third electrode 9, a fourth electrode 10 and a first voltage source 11. The second electrode 8 is adjacent to the first electrode 7. The third electrode 9 is adjacent to the second electrode 8 and the fourth electrode 10 is adjacent to the third electrode 9. The first electrode 7 and the third electrode 9 define a first set of electrodes and are electrically connected. The second electrode 8 and the fourth electrode 10 define a second set of electrodes and are electrically connected. The present invention may employ a plurality of electrodes or sets of electrodes as further discussed below.

The first electrode 7, second electrode 8, third electrode 9 and fourth electrode 10 are positioned to define the nanpore 3. Optional substrate 12 may also comprise the nanopore 3. The first electrode 7, the second electrode 8, the third electrode 9 and the fourth electrode 10 may be positioned or deposited on, or comprise a portion of the optional substrate 12.

The substrate 12 may have a top surface 17 and a bottom surface 19. The substrate 12 may comprise a variety of materials known in the art for designing nanopores. Such materials may comprise silicon, silica, solid-state material such as $Si_3N_4$, carbon based materials, plastics, metals, or other materials known in the art for etching or fabricating semiconductor or electrically conducting materials. The substrate 12 may comprise various shapes and sizes. However, it must be large enough and of sufficient width to be capable of forming the nanopore 3 through it.

The first electrode 7, the second electrode 8, the third electrode 9 and the fourth electrode 10 may comprise a variety of electrically conductive materials. Such materials include electrically conductive metals and alloys of tin, copper, zinc, iron, magnesium, cobalt, nickel, and vanadium. Other materials well known in the art that provide for electrical conduction may also be employed. When the first electrode 7 is deposited on or comprises a portion of the substrate 12, it may be positioned in any location relative to the second electrode 8 and the fourth electrode 10. The electrodes 7, 8, 9 and 10 may be designed in a variety of shapes and sizes.

The first voltage source 11 is electrically connected to the first electrode 7, the second electrode 8, the third electrode 9 and the fourth electrode 10. In certain embodiments each of the electrodes may be spaced along a longitudinal axis with a direct current (DC) voltage and a superimposed radio frequency (RF) potential. The first electrode 7 and the third electrode 9 are connected and define a first set of electrodes and are at the same DC and RF potential, while the second electrode 8 and the fourth electrode 10 are electrically connected and define a second set of electrodes with an opposite DC voltage and RF potential phase shifted by 180 degrees. The invention should not be interpreted to be limited to two sets of electrodes. Other sets of electrodes or a plurality of sets of electrodes would be possible with the present invention. For instance, if the apparatus comprises a set of e.g. four, six, eight or more electrodes, a different design may be employed. For instance, an RF voltage $V\cos\omega\tau$ of amplitude V and frequency $\omega/2\pi$ is applied to the first electrode 7, with alternate electrodes having equal amplitude and opposite phase. However, if the apparatus has four electrodes as discussed above, it can be optionally operated by applying voltages of $U+V\cos\omega\tau$ and $-[U+V\cos\omega\tau]$ to alternate electrodes as is well known in the art for quadrupole mass filters. In that embodiment, U is a DC voltage. U, V and $\omega$ are chosen for given dimensions and biopolymer mass to charge ratio ranges in the manner commonly known in the art for quadrupole mass filters.

As previously described, the nanopore 3 may be positioned anywhere on the substrate 12. The nanopore may range in size from 1 nm to as large as 300 nm. In most cases, effective nanopores for identifying and sequencing biopolymers would be in the range of around 2–20 nms. These size nanopores are just large enough to allow for translocation of a biopolymer. The nanopore 3 may be created using any methods well known in the art. For instance, the nanopore 3, may be sculpted in the substrate 12, using ion argon beam sputtering, etching, photolithography, or other methods and techniques well known in the art.

The biopolymer 5 may comprise a variety of shapes, sizes and materials. For instance, the biopolymer 5 may be a nucleotide, biopolymer, protein, peptide, amino acid, nucleic acid, nucleoside, carbohydrate, glycan, lipid, sphingolipid, proteoglycan, antibody, etc. The shape or size of the molecule is not important, but it must be capable of translocation through the nanopore 3. For instance, both single stranded and double stranded RNA and DNA may be used as a biopolymer 5. In addition, the biopolymer 5 may contain groups or functional groups that are charged. Furthermore, metals or materials may be added, doped or intercalated within the biopolymer 5 to provide a net dipole, a charge or allow for conductivity through the biomolecule.

Referring now to FIG. 1A, a first embodiment of the invention is depicted. The first electrode 7, the second electrode 8, the third electrode 9 and the fourth electrode 10 are all positioned on the top surface 17 of the substrate 12 adjacent to the nanopore 3. The electrode 7 is positioned adjacent to the electrode 8. The electrode 8 is positioned adjacent to the electrode 9. The electrode 9 is positioned adjacent to the electrode 10. Each of the electrodes 7–10 is positioned in the same plane adjacent to the nanopore 3. As described above, the electrode 7 and the electrode 9 are electrically connected to define a first set of electrodes. In addition, the electrode 8 and the electrode 10 are electrically connected to define a second set of electrodes.

Figure 1B:
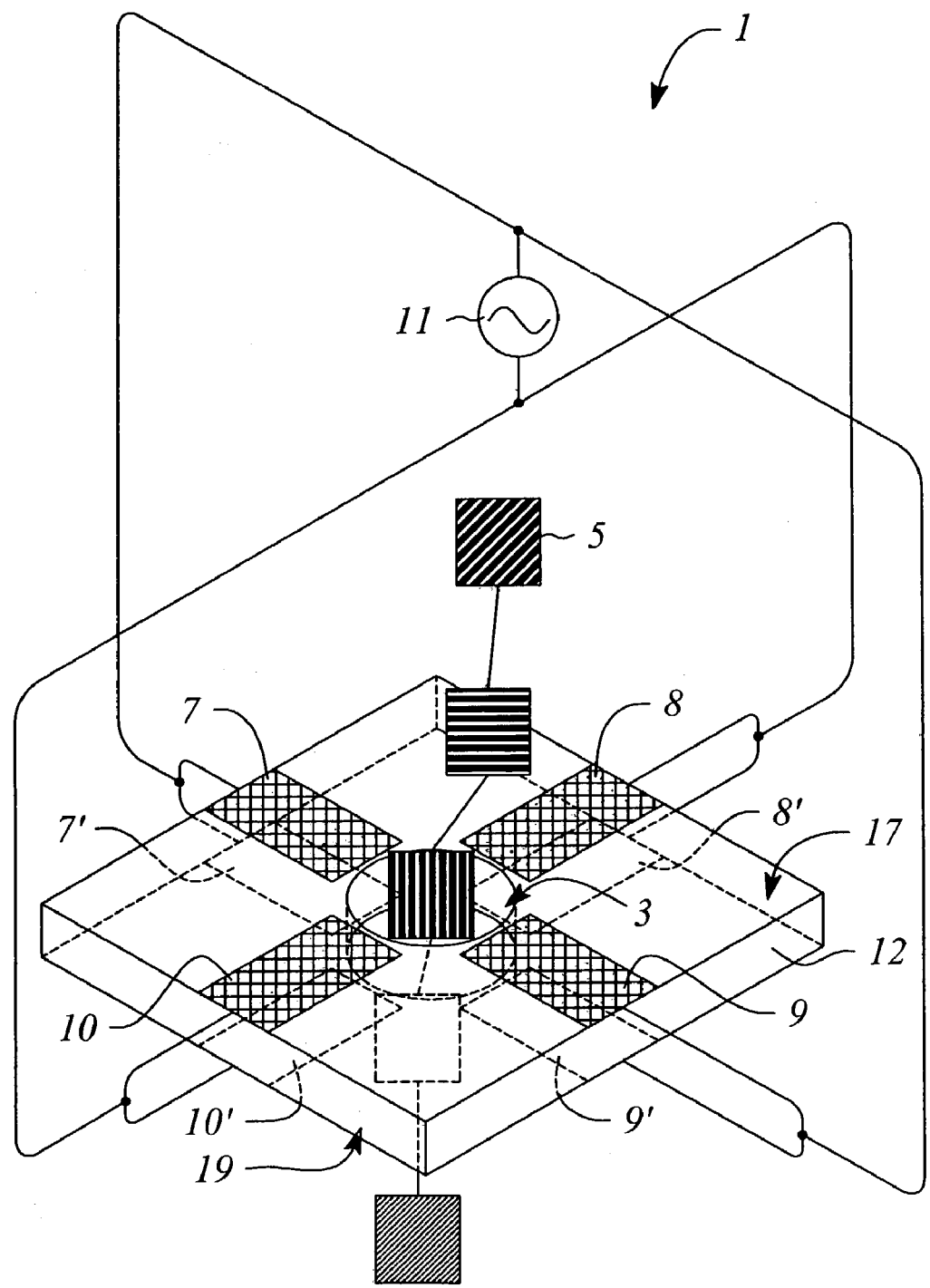
FIG. 1B is a schematic representation of a second embodiment of the present invention.

Referring now to FIG. 1B, a second embodiment of the invention is shown. In this embodiment of the invention, additional electrodes are employed on substrate 12. The additional electrodes include a fifth electrode 7', a sixth electrode 8' adjacent to the fifth electrode 7', a seventh electrode 9' adjacent to the sixth electrode 8' and an eighth electrode 10' adjacent to the seventh electrode 9'. Electrodes 7', 8', 9' and 10' may comprise, be part of or be attached to the substrate 12. In this embodiment of the invention electrodes 7',8', 9' and 10' are positioned on the bottom surface 19 of substrate 12 adjacent to the nanopore 3, wherein each of said electrodes is positioned adjacent to said nanopore 3 to create a quadrupole field through the length of said nanopore 3. The first electrode 7 is electrically connected to the fifth electrode 7'. The second electrode 8 is electrically connected to the sixth electrode 8'. The third electrode 9 is electrically connected to the seventh electrode 9'. The fourth electrode 10 is electrically connected to the eighth electrode 10'. Similar to the design above, the electrodes 7,7' are electrically connected to the 9,9' electrodes to define a first set of electrodes. In addition, the 8,8' and 10, 10' electrodes are electrically connected to define a second set of electrodes.

Figure 2A:
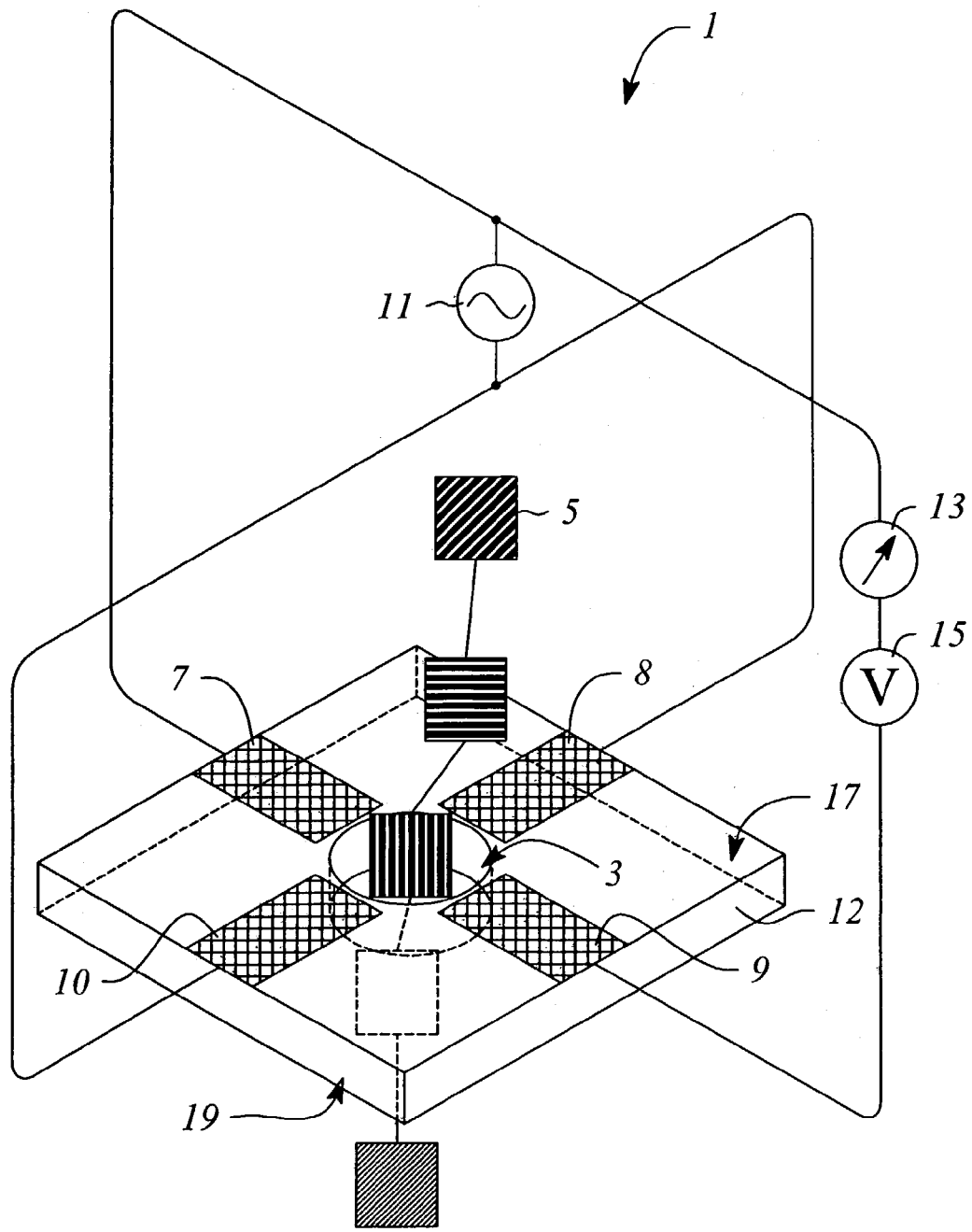
FIG. 2A shows a schematic representation of a third embodiment of the present invention.
Figure 2B:
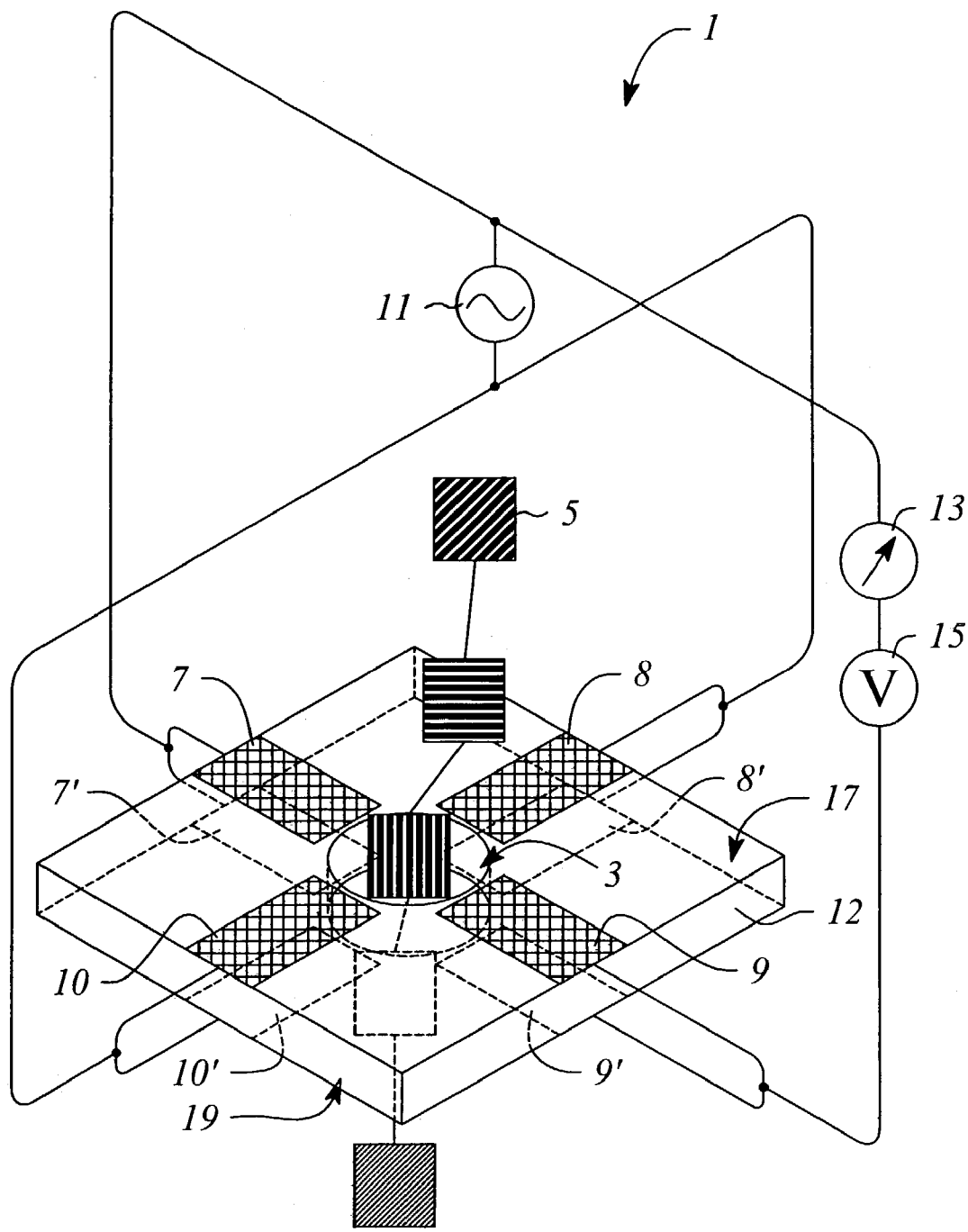
FIG. 2B shows a schematic representation of a fourth embodiment of the present invention.
Figure 3:
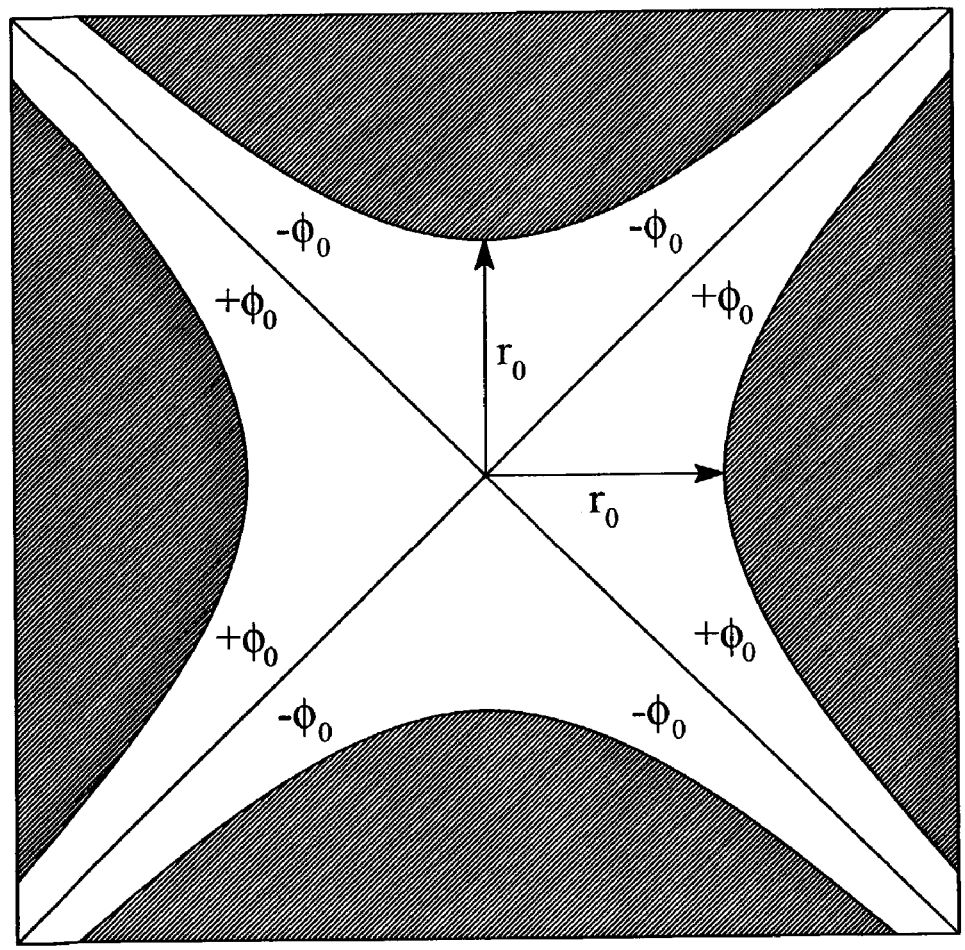
FIG. 3 shows a cross-sectional view of the RF-quadrupole potentials also showing the parameters described in the text.

Referring now to FIGS. 2A and 2B, further embodiments of the present invention are depicted. These embodiments are similar to FIGS. 1A and 1B, but contain a second voltage source 15 coupled to a current measuring device 13 for monitoring quantum tunneling through opposing electrodes and for detection of portions of the biopolymer 5. The second voltage source 15 and current measuring device 13 may be used to monitor quantum tunneling in either a static voltage or ramped voltage mode.

Having now described the apparatus of the invention in detail, a discussion of the method is now in order. The method of the present invention provides a method for controlling the lateral movement of a biopolymer as it translocates a nanopore. The method comprises applying a DC voltage and radio frequency voltage to a first set of electrodes, applying an opposite DC voltage and phase shifted radio frequency voltage to a second set of electrodes to produce an electric field between the first set of electrodes and the second set of electrodes, and controlling the movement of a biopolymer using the electric field as the biopolymer translocates a nanopore. How the actual apparatus and method prevent the lateral movement of a biopolymer will now be described in greater detail.

It is well known that an RF-quadrupole field can be used to focus and guide a charged particle along a specified propagation direction. A typical application of this phenomenon is in the area of mass spectrometry, where devices employing RF-quadrupole fields guide particles of specified charge-to-mass ratios down a propagation channel, and cause particles of different charge-to-mass ratios to be expelled from this region. The specified charge-to-mass ratio is determined by the geometry and parameters of the RF-field. In a typical device, four rods form a quadrupole field in cross-section. As described further in the Appendix, for appropriate parameter choice, the RF field produces an effective potential that tends to force the charged particle toward the central axis. If there are not dissipative effects, the particle travels down this axis with an oscillatory transverse motion under the effects of the transverse effective harmonic potential. If there are dissipative effects, as the particle travels down the propagation axis, the transverse oscillations are damped out, and the trajectory smoothly settles on the axis.

It is possible to exploit this physical phenomenon to control biopolymers that are translocating a nanopore, and smoothly guide them to the center of the pore. FIGS. 1–2 show the apparatus of the present invention that is used to implement this effect. The set of four electrodes is used to create an approximate quadrupole field in the nanopore opening. The RF-field parameters (to be discussed later) are chosen to guide particles with the charge-to-mass ratio of the biopolymers. The effective potential generated provides a continuous force guiding the translocating strand to the center of the nanopore. This mitigates the set of problems catalogued above. In particular, restriction of lateral movement allows an unimpeded uniform translocation, as well as symmetric and controlled tunneling current environment. It should be noted that optionally, a DC tunneling voltage can be superimposed upon an opposing pair of electrodes that contribute to generating the quadrupole field.

A physical system that consists of a charged bipolymer strand passing through an RF quadrupole field, which is of limited extent in the propagation direction, is clearly different from the physical systems described by the prior art. However, it is equally clear that the physical mechanisms generating the effective restoring forces that guide the moving particle toward the axis are the same. Equations (A6) and (A7) in the Appendix describe the transverse forces on the charged particle or a segment of a charged biopolymer strand. For the single particle, it describes the transverse forces as it travels down the length of the device. For the biopolymer, it describes the restoring force exhibited on the moving strand at a fixed spatial point.

Equation (A10) can be used to estimate the RF-voltage parameters required to have the effective forces generate net focusing for a biopolymer strand. Assuming that the DC voltage is zero ($a_u=0$), it is seen from the stability plot (FIG. 4), that it is required that $q_u<0.91$ to have stable trajectories, or net focusing $$0.91 > q_u = \frac{4e}{mr_0^2\Omega^2}V \qquad (1)$$

where e is the electronic charge, m is the effective mass of the relevant portion of the biopolymer strand, $r_o$ is the radius of the quadrupole aperture, $\Omega$ and V are the angular frequency and amplitude of the RF voltage, respectively. The current nanopores would support an $r_o$ of approximately 10 angstroms. A typical nucleotide base has a mass of roughly 400 amu, although the effective mass for a base that is part of a continuous strand would be significantly larger, and depend upon the rigidity of the total structure. For estimation purposes it will be assumed that the effective mass is approximately five times that of an individual base. With these parameter values, the requirement for stability (focusing) as expressed in the equation (1) is given by $$\frac{V}{F^2} < 2 \times 10^{-10} \qquad (2)$$

where V is given in volts and F is the RF frequency in MHz. For an applied RF frequency of 1.0 GHz, the quadrupole would tend to guide the polynucleotide strand toward the center of the nanopore for an RF voltage amplitude satisfying the constraint $$V \leq 200\ \mu V. \qquad (3)$$

The RF-voltage parameters are achievable for the configurations previously described. The present invention is designed to obviate the previously discussed problems. When operated in the guiding (stable) mode, the quadrupole fields force the biopolymer toward the center of the nanopore. This mitigates the problem of non-uniform translocation events due to intermittent interaction of the biopolymer with the nanopore walls. It also greatly improves the detection of the portion of the biopolymer being analyzed by minimizing the effects of variable ionic current flow due to random changes in the shape of the partially blocked pore. These random changes are largely due to lateral offsets of the biopolymer during translocation. For an electron tunneling detection scheme, confining the biopolymer to the center of the nanopore will eliminate the potentially large swings in the magnitude of the measured current by minimizing the variability of the proximity of the biopolymer to the tunneling electrodes.

Figure 4:
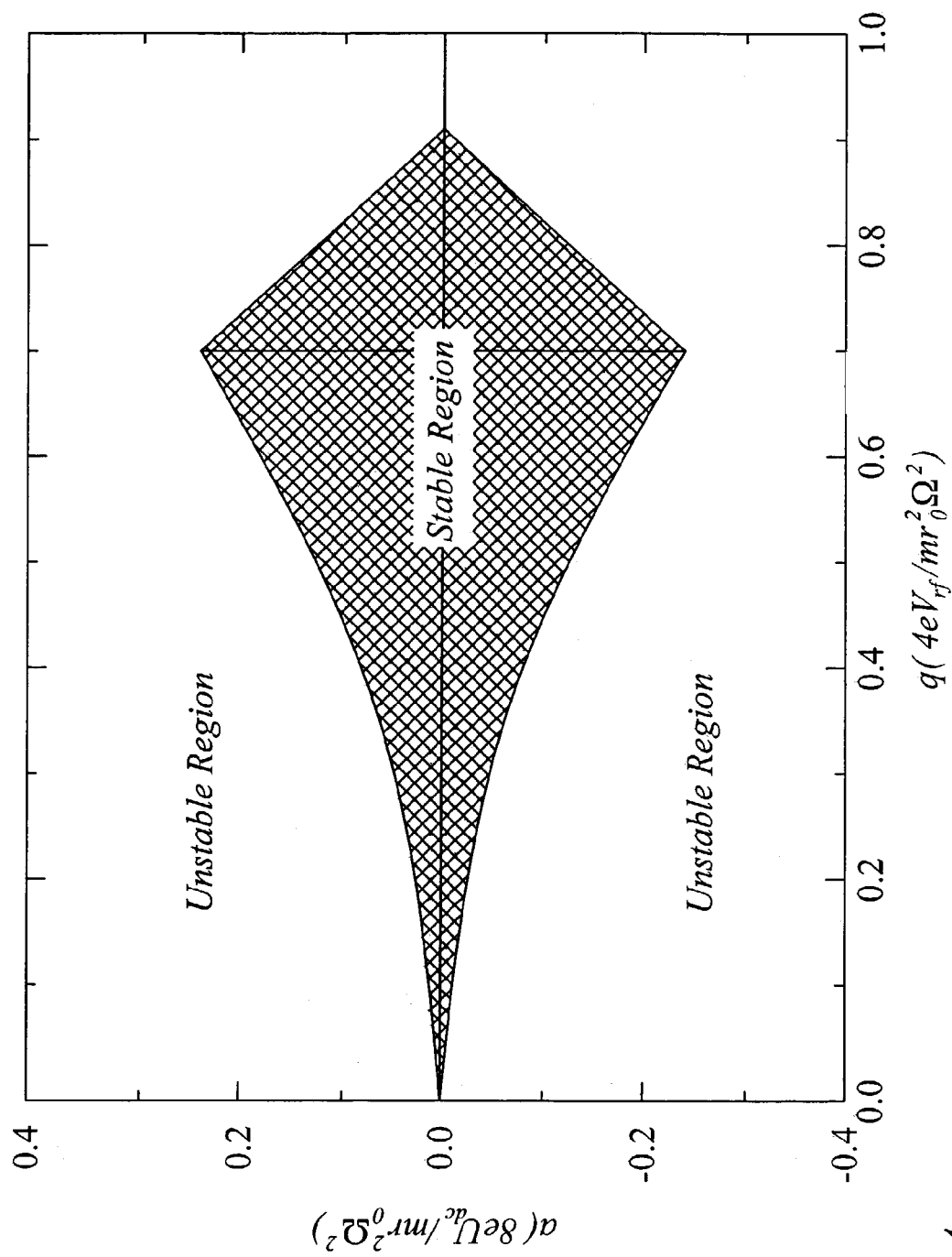
FIG. 4 shows a stability diagram of the Mathieu equation solutions as a function of the parameters $a_u$ and $q_u$.
Figure 5:
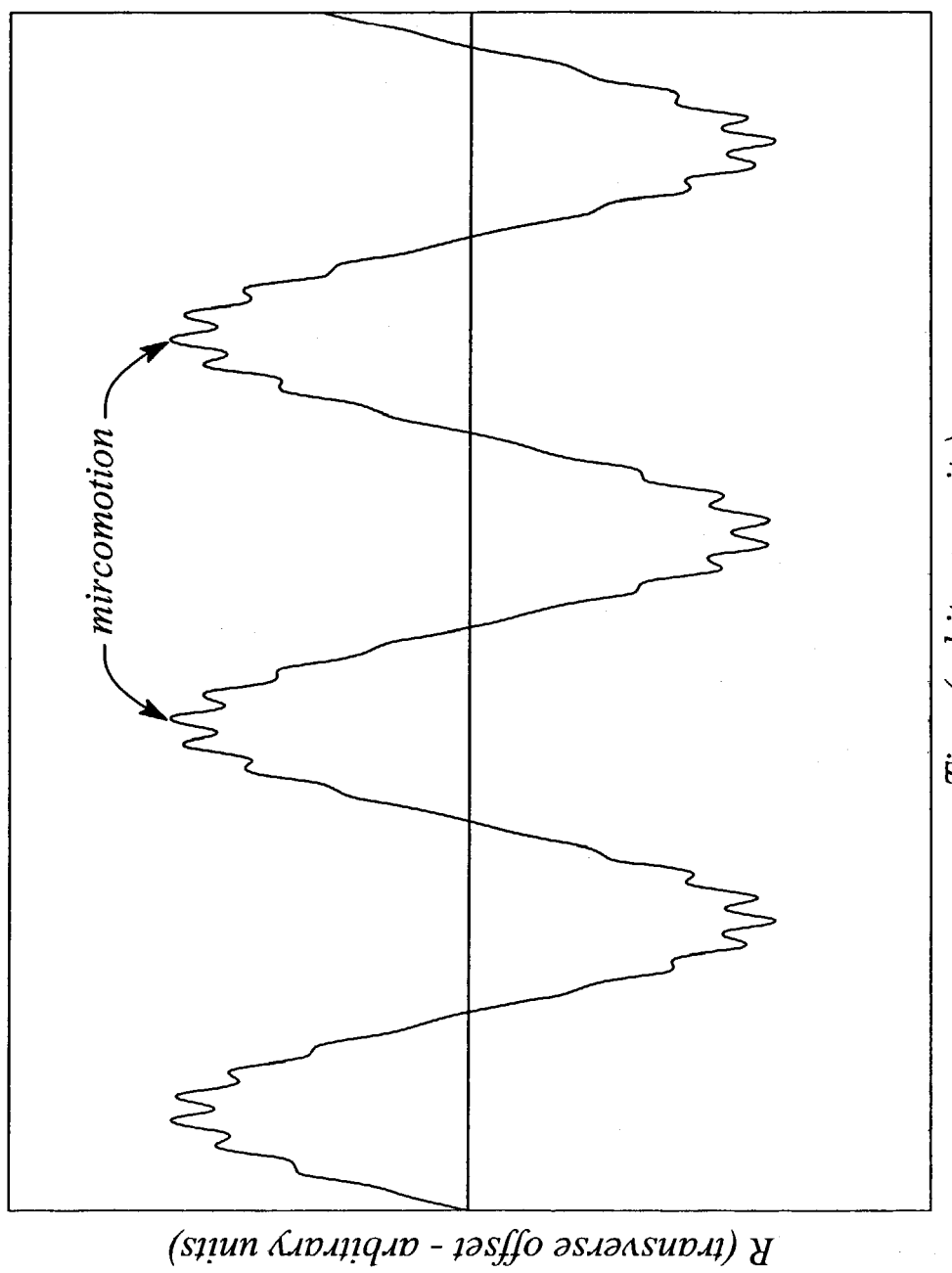
FIG. 5 shows a typical solution of the Mathieu equation for parameter choices that generate a stable trajectory. The component micromotion and macromotion are more clearly shown.

Another use of the present invention quadrupole structure is based upon operating the quadrupole with parameters chosen to have the strand dynamics to be in the unstable regime, as defined in FIG. 4. For the parameters specified in the example described above, this would correspond to adjusting the amplitude of the RF-voltage above the level of the equation (3), i.e.

$$V > 200\ \mu V. \qquad (4)$$

For this voltage, the lateral motion of the translocating biopolymer would be unstable, forcing it away from the center of the nanopore. For appropriate parameter choices, this would "pin" the biopolymer against the wall of the nanopore. Depending upon the structure of the nanopore walls, this could cause the translocation process to be halted in a controlled fashion. This ability to stop and resume translocation of the biopolymer in a controlled way has a number of useful applications. It could be used to slow down the rate of translocation, allowing more time for the base detection measurements. It could also be used to hold a portion of the biopolymer in place while the measurement was allowed to focus on one particular portion of the biopolymer.

Although the invention is shown in FIG. 1 and FIG. 2, the invention is not limited to these particular embodiments. Other embodiments and structures are possible. For instance, the electrodes may have any generalized shape that produces approximate quadrupole fields in the nanopore. Also, to increase the length of the region over which the quadrupole-biopolymer interaction occurs, multiple electrode sets can be employed. For example, electrode sets can be used on both sides of the nanopore, causing the quadrupole field to be more accurately maintained over the entire length of the nanopore. Additionally, higher multipole fields can be used, such as octupole fields. These embodiments have stability diagrams similar to the one described above and can be exploited in similar ways. This is the case even if the stability diagrams of these embodiments are less sharply defined.

EXAMPLE 1

An example of the described device could be fabricated using techniques known to those skilled in the art. For instance, the nanopore can be made in a thin (500 nm) freestanding silicon nitride ($SiN_3$) membrane supported on a silicon frame. Using a focused Ion Beam (FIB) machine, a single initial pore of roughly 500 nM diameter can be created in the membrane. Then, illumination of the pore region with a beam of 3 KeV Argon ion sputters material and slowly closes the hole to the desired dimension of roughly 2 nM in diameter (See Li et al., Nature, 412: 166–169, 2001). Metal electrodes are formed by patterning and evaporation, or other deposition means, to generate the quadrupole structure. Wire bonding to the metal electrodes allows connection to the RF voltage source. The RF voltage source has the modest requirements of several hundred microvolts at a frequency of 1.0 GHz.

EXAMPLE 2

A second example of the present invention would be similar to the first, however, and additional set of four electrodes are deposited on the opposing face of the substrate. The second set of electrodes are wired bonded in parallel to the RF voltage source, allowing coherent generation of the quadrupole fields over the length of the nanopore.

We claim:

1. A biopolymer translocation apparatus for controlling lateral movement of a biopolymer as it translocates through a nanopore, comprising:
    (a) a first electrode;
    (b) a second electrode adjacent to said first electrode;
    (c) a third electrode adjacent to said second electrode, said third electrode being in electrical connection with said first electrode and defining a first set of electrodes;
    (d) a fourth electrode adjacent to said third electrode, said fourth electrode being in electrical connection with said second electrode and defining a second set of electrodes, wherein said first-electrode, said second electrode, said third electrode and said fourth electrodes define a nanopore wherein the nanopore is between the first and third electrodes and between the second and fourth electrodes;
(e) a first voltage source for applying voltages to the first, second, third and fourth electrodes for producing an electric field for controlling lateral movement of said biopolymer as it translocates through said nanopore; and
(f) a second voltage source and a current measuring device in electrical connection with said first and third electrodes for monitoring quantum tunneling through said biopolymer and said first and third electrodes.

2. The apparatus as recited in claim 1, wherein said first voltage source applies a direct current (DC) to at least one electrode.

3. The apparatus as recited in claim 1, wherein said first voltage source applies alternating current (AC) to at least one electrode.

4. The apparatus as recited in claim 1, wherein said first voltage source applies direct current (DC) and alternating current (AC) to at least one electrode.

5. The apparatus as recited in claim 1, further comprising a substrate on which said first electrode is disposed.

6. The apparatus as recited in claim 1, further comprising a substrate on which said second electrode is disposed.

7. The apparatus of claim 1, further comprising a substrate on which said third electrode is disposed.

8. The apparatus of claim 1, further comprising a substrate on which said fourth electrode is disposed.

9. The apparatus of claim 1, wherein said biopolymer is a charged polymer.

10. The apparatus of claim 1, wherein said biopolymer is selected from the group consisting of carbohydrates, proteins, nucleic acids, lipids, glycans, biopolymers, proteoglycans and polypeptides.

11. An apparatus as recited in claim 1, further comprising a substrate having a top surface and a bottom surface, said first electrode, second electrode third electrode and fourth electrode being positioned on said top surface of said substrate.

12. A biopolymer translocation apparatus for controlling lateral movement of a biopolymer as it translocates through a nanopore, comprising:
(a) a first electrode;
(b) a second electrode adjacent to said first electrode;
(c) a third electrode adjacent to said second electrode, said third electrode being in electrical connection with said first electrode and defining a first set of electrodes;
(d) a fourth electrode adjacent to said third electrode, said fourth electrode being in electrical connection with said second electrode and defining a second set of electrodes, wherein said first-electrode, said second electrode, said third electrode and said fourth electrodes define a nanopore there between;
(e) a first voltage source for applying voltages to said electrodes for producing an electric field for controlling lateral movement of said biopolymer as it translocates through said nanopore;
a fifth electrode, a sixth electrode adjacent to said fifth electrode, a seventh electrode adjacent to said sixth electrode and an eighth electrode adjacent to said seventh electrode, said fifth electrode being in electrical connection with said first electrode, said sixth electrode being in electrical connection with said second electrode, said third electrode being in electrical connection with said seventh electrode and said fourth electrode being in electrical connection with said eighth electrode, wherein each of said electrodes are positioned adjacent to said nanopore to create a quadrupole field through the length of said nanopore.

13. A biopolymer translocation apparatus for controlling lateral movement of a biopolymer as it translocates through a nanopore, comprising:
(a) a first electrode;
(b) a second electrode adjacent to said first electrode;
(c) a third electrode adjacent to said second electrode, said third electrode being in electrical connection with said first electrode and defining a first set of electrodes;
(d) a fourth electrode adjacent to said third electrode, said fourth electrode being in electrical connection with said second electrode and defining a second set of electrodes, wherein said first-electrode, said second electrode, said third electrode and said fourth electrodes define a nanopore there between;
(e) a first voltage source for applying voltages to said electrodes for producing an electric field for controlling lateral movement of said biopolymer as it translocates through said nanopore;
a substrate having a top surface and a bottom surface, said first electrode, second electrode, third electrode and fourth electrode being positioned on said top surface of said substrate;
a fifth electrode, a sixth electrode adjacent to said fifth electrode, a seventh electrode adjacent to said sixth electrode and an eighth electrode adjacent to said seventh electrode, said fifth electrode being in electrical connection with said first electrode, said sixth electrode being in electrical connection with said second electrode, said third electrode being in electrical connection with said seventh electrode and said fourth electrode being in electrical connection with said eighth electrode, wherein each of said electrodes are positioned adjacent to said nanopore to create a quadrupole field through the length of said nanopore, said fifth electrode, sixth electrode, seventh electrode and eighth electrode being positioned on said bottom surface of said substrate.

14. A biopolymer translocation apparatus for controlling lateral movement of a biopolymer as it translocates through a nanopore, comprising:
(a) a first electrode;
(b) a second electrode adjacent to said first electrode;
(c) a third electrode adjacent to said second electrode, said third electrode being in electrical connection with said first electrode and defining a first set of electrodes;
(d) a fourth electrode adjacent to said third electrode, said fourth electrode being in electrical connection with said second electrode and defining a second set of electrodes, wherein said first-electrode, said second electrode, said third electrode and said fourth electrodes define a nanopore there between;
(e) a first voltage source for applying voltages to said electrodes for producing an electric field for controlling lateral movement of said biopolymer as it translocates through said nanopore;
(f) a second voltage source and a current measuring device in electrical connection with said first and third electrodes for monitoring quantum tunneling through said biopolymer and said first and third electrodes; and
(g) a fifth electrode, a sixth electrode adjacent to said fifth electrode, a seventh electrode adjacent to said sixth electrode and an eighth electrode adjacent to said seventh electrode, said fifth electrode being in electrical connection with said first electrode, said sixth electrode being in electrical connection with said second electrode, said third electrode being in electrical connection with said seventh electrode and said fourth electrode being in electrical connection with said eighth electrode, wherein each of said electrodes are positioned adjacent to said nanopore to create a quadrupole field through the length of said nanopore.

15. A biopolymer translocation apparatus for controlling lateral movement of a biopolymer as it translocates through a nanopore, comprising:
    (a) a first electrode;
    (b) a second electrode adjacent to said first electrode;
    (c) a third electrode adjacent to said second electrode, said third electrode being in electrical connection with said first electrode and defining a first set of electrodes;
    (d) a fourth electrode adjacent to said third electrode, said fourth electrode being in electrical connection with said second electrode and defining a second set of electrodes, wherein said first-electrode, said second electrode, said third electrode and said fourth electrodes define a nanopore there between;
    (e) a first voltage source for applying voltages to said electrodes for producing an electric field for controlling lateral movement of said biopolymer as it translocates through said nanopore;
    (f) a second voltage source and a current measuring device in electrical connection with said first and third electrodes for monitoring quantum tunneling through said biopolymer and said first and third electrodes;
    (g) a substrate having a top surface and a bottom surface, said first electrode, second electrode, third electrode and fourth electrode being positioned on said top surface, of said substrate; and
    (h) a fifth electrode, a sixth electrode adjacent to said fifth electrode, a seventh electrode adjacent to said sixth electrode and an eighth electrode adjacent to said seventh electrode, said fifth electrode being in electrical connection with said first electrode, said sixth electrode being in electrical connection with said second electrode, said third electrode being in electrical connection with said seventh electrode and said fourth electrode being in electrical connection with said eighth electrode, wherein each of said electrodes are positioned adjacent to said nanopore to create a quadrupole field through the length of said nanopore, said fifth electrode, sixth electrode, seventh electrode and eighth electrode being positioned on said bottom surface of said substrate.

* * * * *